(12) United States Patent
Goldman

(10) Patent No.: US 6,311,346 B1
(45) Date of Patent: Nov. 6, 2001

(54) TRANSFER BELT

(76) Inventor: Heidi Goldman, P.O. Box 255, Helena, MT (US) 59624

( * ) Notice: Subject to any disclaimer, the term of this patent is extended or adjusted under 35 U.S.C. 154(b) by 0 days.

(21) Appl. No.: 09/525,560

(22) Filed: Mar. 15, 2000

Related U.S. Application Data

(60) Provisional application No. 60/125,699, filed on Mar. 23, 1999.

(51) Int. Cl.[7] .................. A61G 7/10; A61F 5/37
(52) U.S. Cl. ............... 5/81.1 T; 5/89.1; 128/876
(58) Field of Search .................. 5/81.1 T, 89.1; 128/96.1, 876; 294/140; 2/311, 312, 322, 338

(56) References Cited

U.S. PATENT DOCUMENTS

| | | | |
|---|---|---|---|
| 5,065,773 | * 11/1991 | Jackson et al. | 128/876 |
| 5,158,098 | * 10/1992 | Jalalian | 128/876 |
| 5,647,378 | * 7/1997 | Farnum | 5/81.1 T |
| 5,711,044 | * 1/1998 | Newman et al. | 5/81.1 T |
| 5,896,859 | * 4/1999 | Carroll | 128/845 |
| 6,073,280 | * 6/2000 | Farnum | 5/81.1 T |

FOREIGN PATENT DOCUMENTS

2213734-A * 8/1989 (GB) ..................... 5/89.1

* cited by examiner

Primary Examiner—Michael F. Trettel
(74) Attorney, Agent, or Firm—Jerry Johnson

(57) ABSTRACT

A transfer belt is provided that includes two elongated pads. The pads are disposed on the belt proximate to both sides of the wearer. The pads minimize discomfort for the wearer by ensuring that forces applied on the belt are applied through a surface area that is much larger than that of the belt and through a cushioning pad which is much softer than the belt. The addition of the pads greatly increases the safety of using a transfer belt on a patient. The pads also provide an increase in the comfort and safety for the medical or care taking assistant during the use of the transfer belt. This comfort and safety is provided by the presence of a gap between the belt and the belt wearer within which the medical or care taking assistant can place their hand.

8 Claims, 2 Drawing Sheets

TRANSFER BELT

RELATED APPLICATIONS

The present invention claims the benefit under Title 35, United States Code, Section 119E of the United States Provisional Application Ser. No. 60/125,699 filed Mar. 23, 1999 entitled "Adjustable Pad Cushions" now lapsed.

BACKGROUND

Transfer belts, also known as gait belts, are secured around the waist of invalids and other medical patients having mobility difficulties. The transfer belt allows a medical assistant or care taking assistant to assist the movement of the patient by providing a belt which can be grasped by the assistant.

Specifically, the transfer belt is secured tightly around the waist of the patient by a care taking assistant or medical assistant. The belt provides a loop which when grasped by the assistant allows the assistant to assist the movement of the patient by applying forces to the patient. Such forces are transferred through the belt. Through the belt, the assistant can apply a significant force on the patient. The forces which may be applied by the assistant through the belt include lifting forces, stabilizing forces, guidance forces. Patient movements which may be assisted by the medical assistant include walking, sitting, standing, etc.

The transfer belt needs to be sufficiently tightly secured around the patient so that a force applied to the patient through the belt will accomplish the intended result. The belt also needs to be tight to minimize movement of the belt in relation to the patient. A belt moving under applied forces will cause significant discomfort to the patient. Therefor, the belt must be maintained around the waist in a very tight condition which is often uncomfortable for the patient.

Once the belt is sufficiently tightened around the patient, the belt becomes more difficult to grasp by the assistant. When grasping the belt, the assistant and the patient often experience discomfort from the placement of the hand between the tightened belt and the patient.

Accordingly, there is a need for a transfer belt that can be tightly secured around the waist of a patient but which minimizes the discomfort to the patient and the assistant when the belt is grasped by the assistant. There is also a need for a belt which increases the overall comfort and safety to the patient. There is a further need for a belt which provides these benefits which is inexpensive in cost.

SUMMARY

The present invention satisfies the previously mentioned needs by providing a transfer belt that includes two elongated pads. The pads minimize discomfort for the wearer by ensuring that forces applied on the belt are applied through a surface area that is much larger than that of the belt and through a cushioning pad which is much softer than the belt. The addition of the pads greatly increases the comfort and safety of using a transfer belt on a patient. The pads also provide an increase in the comfort and safety for the medical or care taking assistant during the use of the transfer belt. This comfort and safety is provided by the presence of a gap between the belt and the belt wearer.

DRAWINGS

Figure 4:
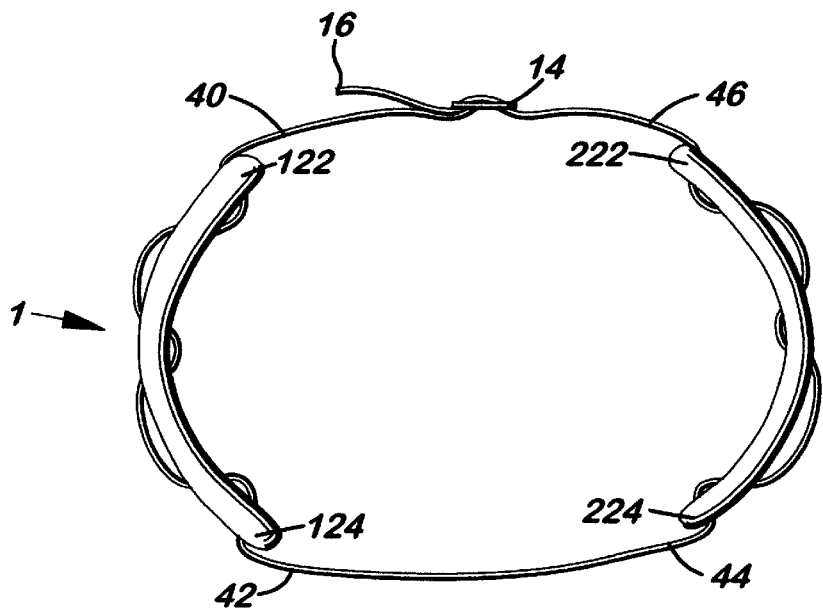

FIG. 4 shows a top view of one version of the transfer belt of the present invention. The transfer belt is shown disposed around the waist of a patient shown in cross section. Gaps separating the belt from the patient are clearly shown in this figure.

DESCRIPTION

Figure 1:
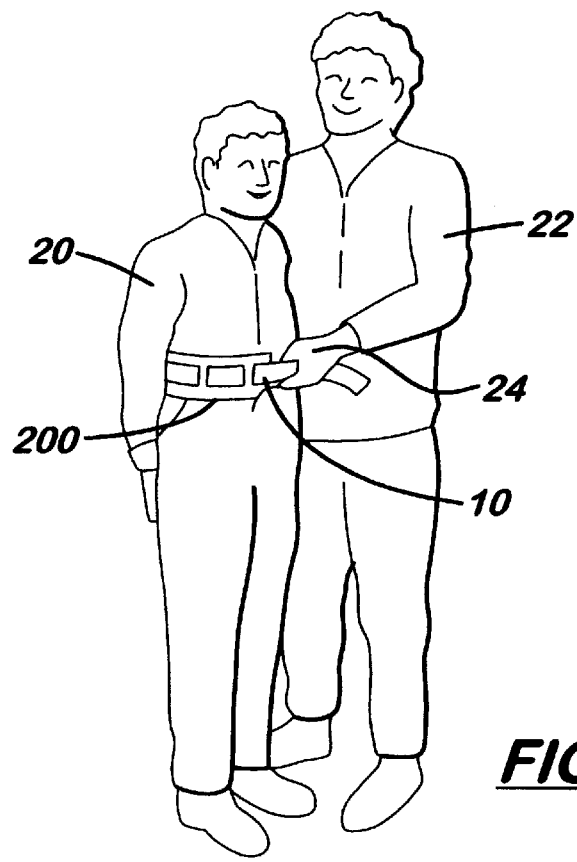
FIG. 1 shows a front view of a patient wearing a version of the transfer belt of the present invention, and a patient's assistant.

FIG. 1 shows a front view of a patient wearing a version of the transfer belt of the present invention, and a patient's assistant. The patient's assistant is grasping the belt with her left hand at a position immediately in front of a pad disposed on the belt at a position which is proximate to the right side of the patient. As will be described further, the left hand of the patient's assistant is disposed immediately in front of the pad. At this location, proximate to where the belt is overlapped over the outside surface of the pad, a gap is formed between the belt and the pad. The assistant's hand is inserted through this gap such that the assistant may directly grasp the belt. The assistant should not use the pads as a hand hold. The gap ensures that the hand grasping the belt at this location is comfortable, and also ensures that the patient is not discomforted by the placement of the assistant's hand next to his or her body. Although not shown in this figure, the assistant's right hand is disposed proximate to the center of the patients back between the right side pad and a left side pad which is also not shown in this figure. The hand positions of the patient's assistant is one of a variety of positions permitted by the present invention. In the position shown, as in other possible positions, the patient's assistant is able to maintain a safe hold on the patient by grasping the transfer belt. Any forces that the patient's assistant applies to the belt are transferred to the patient through the cushioning pads. Accordingly, the pads distribute these forces over a large area which ensures comfort and safety for the patient.

Figure 2:
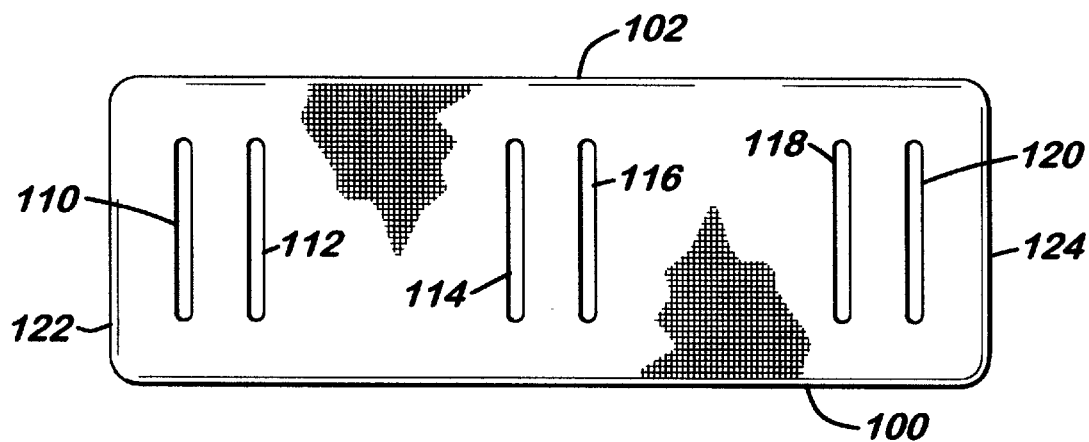
FIG. 2 shows a version of the pad for use within the transfer belt of the present invention.

FIG. 2 shows a version of the pad incorporated into transfer belt of the present invention. The pad includes an elongate body 100 made of sponge rubber foam, open cell foam sponge, or other flexible, compressible material such as Rubbatex and Neoprene which provide the desired cushioning, and durability. The approximate size of the pad is 10¼ inches by 3¼ inches, although it is understood that a variety of sizes could be used. The thickness of the pad is typically between ⅛ inch and ½ inch.

The body 100 includes a series of paired slots 110 and 112, 114 and 116, and 118 and 120. The slots have a length of approximately 2¼ inches which corresponds to slightly larger than the width of the typical transfer belt. The transfer belt is threaded through each pair of slots which secures the pad to the belt, yet allows the pad to slide relative to the belt for adjustment purposes. The pad includes a first side edge 122 and an opposite second side edge 124.

Figure 3:
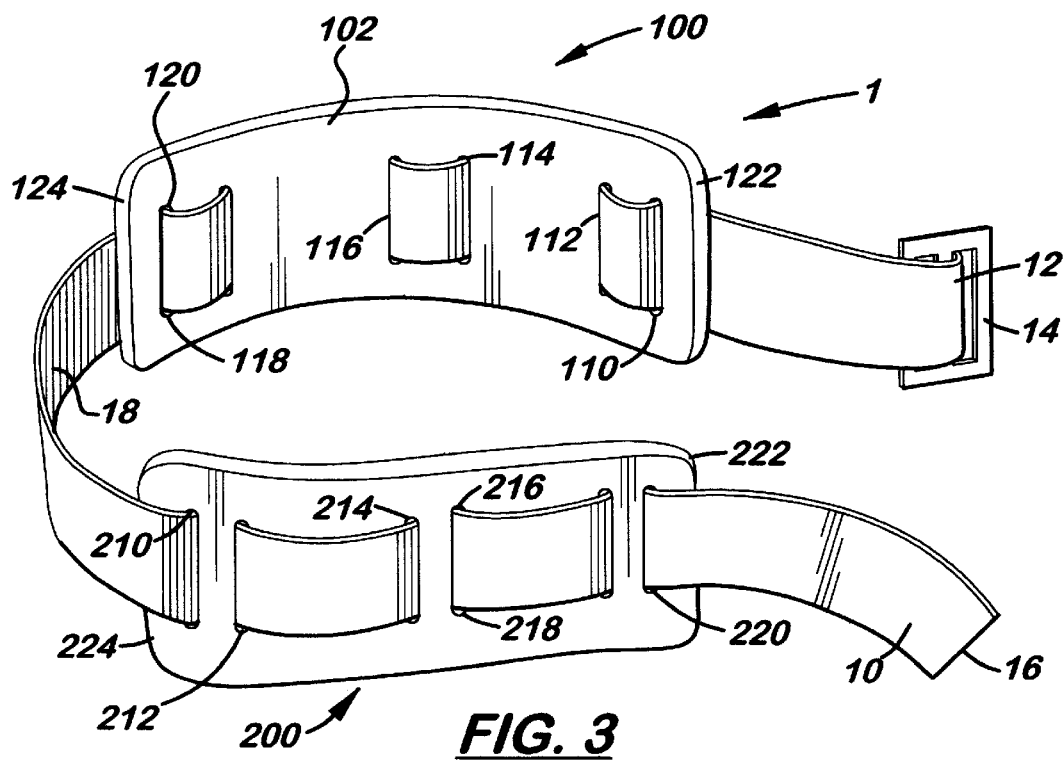
FIG. 3 shows a side view of the assembled transfer belt of one version of the present invention.

FIG. 3 shows the assembled transfer belt 1 of one version of the present invention. The cushion pad 100 of FIG. 2, as well as cushion pad 200, both of which are disposed on the belt 10. The cushion pad 200 in this version of the invention is identical to cushion pad 100. It would be possible, however, to use two pads of different shapes or sizes to accommodate specific patient needs. The belt 10 includes a first end 12. An adjustable closure assembly comprising a buckle 14 is disposed on the first end 12. The belt further includes a second end 16 and a mid section 18 which is intermediate the first end 12 and the second end 16. The buckle shown is one of many commercially available buckles which may be used to secure the first end of the belt to a selected point on the belt mid section proximate to the second end. The second end of the belt has been threaded through the three pairs of slots on each pad. This arrangement allows the pads to slide relative to the belt so that adjustments to the pad position relative to the patient may be easily made. The belt mid section overlaps both pads at the first and second ends of the pads. The importance of this overlap was described in FIG. 1, and will be further shown in FIG. 4.

FIG. 4 shows the version of the transfer belt 1 of the present invention, as was shown in FIGS. 1 through 3. The transfer belt i is shown as a loop which is how the belt would be disposed around the waist of a patient. The figure shows the typical placement of the two pads of the transfer belt disposed adjacent to the patient's sides. FIG. 4 further illustrates four hand locations 40, 42, 44, and 46, which are located on the belt at locations proximate to the side edges the pads. The four hand locations are areas where the belt is spaced from the user by a distance equal to the thickness of the pad. As has been described, at these locations a gap is created between the belt and the patient which allows an assistant's hand to be inserted beneath the belt while the assistant grasps the belt. The spaced apart relationship of the belt to the patient at these locations minimizes the discomfort caused to the patient and to the assistant, while the assistant's hand is disposed between the belt and the patient.

It is understood that various modifications and changes inform and detail could readily be made without departing from the spirit of the invention. It is therefore intended that the invention be not limited to the exact form and detail herein shown and described, nor to anything less than the whole of the invention herein disclosed and hereinafter claimed.

What is claimed is:

1. A patient transfer belt adapted for use around the waist of a patient comprising:
    an adjustable waist belt having first and second ends, and a belt mid section intermediate the first and second ends;
    an adjustable closure assembly disposed on the first end of the belt for securing the belt into a loop with the first end secured to a predetermined location on the mid section proximate to the second end;
    the belt further including an inside surface for looping around the waist of a patient, and an outside surface;
    a first cushioning pad disposed on the belt mid section proximate to the first end;
    a second cushioning pad disposed on the belt mid section proximate to the second end;
    means for securing the first and second pads to the belt; wherein the means for securing the first and second pads to the belt allow the pads to slide relative to the belt;
    wherein the first and second pads both include an inside and an outside surface; the inside surface facing the waist of the patient, the outside surface facing away from the patient;
    wherein the first pad includes a first side edge proximate to the first end of the belt and a second side edge; and, wherein the second pad includes a first side edge proximate to the second end of the belt and a second side edge;
    wherein the inside surface of the belt mid section overlaps the side edges of both pads, and wherein the belt inside surface at locations proximate to the side edges of the pads, but not overlapping the pads, is subsequently disposed at a spaced apart distance from the inside surface of the belt; and,
    wherein the transfer belt at the locations proximate to the side edges of the pads, but not overlapping the pads, is adapted for providing hand grasping positions, such that a hand may be easily placed within the spaced apart distance separating the inside surface of the belt and the waist of the patient.

2. The transfer belt of claim 1, wherein the second ends of the pads are disposed proximate to each other and are separated from each other by a portion of the belt mid section.

3. The transfer belt of claim 1, wherein the pads have an elongated shape having a predetermined length and width, and wherein the width is wider than the belt.

4. The transfer belt of claim 1, wherein the means for securing the first and second pads to the belt comprises at least two slots disposed within each pad; and, wherein the belt passes through each slot.

5. The transfer belt of claim 4, wherein each pad includes six slots.

6. The transfer belt of claim 5, wherein the slots are disposed on the pad in three closely spaced apart pairs.

7. The transfer belt of claim 1, wherein the pads are constructed of a flexible compressible material.

8. The transfer belt of claim 1, wherein the means for securing the first and second pads to the belt comprises at least two slots disposed within each pad; and, wherein the belt passes through each slot; and, wherein the pads are slidingly engaged on the belt allowing repositioning of the pads on the belt.

* * * * *